United States Patent [19]

Ueda et al.

[11] Patent Number: 5,026,835
[45] Date of Patent: Jun. 25, 1991

[54] PYRIMIDINE 2'-METHYLIDENE NUCLEOSIDE COMPOUNDS

[75] Inventors: Tohru Ueda, Sapporo; Takuma Sasaki, Kanazawa; Akira Matsuda, Sapporo; Takanori Miyashita; Shinji Sakata, both of Choshi, all of Japan; Keiji Yamagami, Baltimore, Md.; Akihiro Fujii, Kiyose, Japan

[73] Assignees: Yamasa Shoyu Co., Ltd., Chiba; Yoshitomi Pharmaceutical Industries, Ltd., Osaka, both of Japan

[21] Appl. No.: 447,512

[22] Filed: Dec. 7, 1989

[30] Foreign Application Priority Data

Dec. 7, 1988 [JP] Japan .................. 63-310865

[51] Int. Cl.$^5$ .............................................. C07H 19/00
[52] U.S. Cl. ......................................... 536/23; 536/24
[58] Field of Search ................................. 536/23, 24

[56] References Cited

FOREIGN PATENT DOCUMENTS 0310673 4/1989 European Pat. Off. .

OTHER PUBLICATIONS

Takenuki et al., "Journal of Medicinal Chemistry", vol. 31, No. 6, pp. 1063-1064 (1988).
Chem. Abstr., 110, 160409h (1989).

Primary Examiner—Johnnie R. Brown
Assistant Examiner—James Oliver Wilson
Attorney, Agent, or Firm—Wenderoth, Lind & Ponack

[57] ABSTRACT

Pyrimidine 2'-deoxy-2'-methylidene nucleoside compounds:

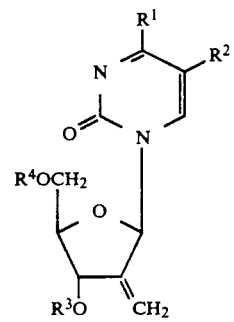

wherein $R^1$ represents amino, hydroxy, silylamino, silyloxy, acylamino or acyloxy; $R^2$ represents hydrogen, halogen, a lower alkyl, a lower alkenyl, a lower alkynyl or haloalkyl; $R^3$ and $R^4$ represent the same or different hydrogen, silyl, acyl or aminoacyl, or a pharmaceutically acceptable salt or hydrate thereof, except that $R^1$ is amino or hydroxy, and both of $R^3$ and $R^4$ are hydrogen.

Said compounds possess excellent antitumor and antiviral activities, thus providing novel anticancer and antiviral agent.

2 Claims, No Drawings

PYRIMIDINE 2'-METHYLIDENE NUCLEOSIDE COMPOUNDS

BACKGROUND OF THE INVENTION

This invention relates to novel pyrimidine 2'-methylidene nucleosides possessing an excellent antitumor and antiviral activities, their pharmaceutically acceptable salts.

Under the circumstances in which death due to cancer has increased in number, chemotherapy and immunotherapy in addition to surgical therapy have been widely conducted. In this connection, in chemotherapy, cytarabine (cytosine arabinoside), 5-fluorouracil and the like as antimethabolites, which are considered effective against acute leukemia, have been clinically used.

In recent years, the development of preventives and remedies for various viral infections has attracted particular attention with the advance of researches into pathogenic viruses. Antiviral agents for use in chemotherapy heretofore proposed for clinical purposes are idoxuridine, cytarabine, vidarabine, acyclovir and like. (See, for example, Yutaka Mizushima and Teramasa Miyamoto, The Edition of 1986, "Konnichi no Chiryoyaku (Present-Day Remedies), Kaisetsu to Binran (Explation and Manual)", Nanko-do, pp. 47-50 (Mar. 10, 1986).)

Furthermore, in European Patent Application 0 310 673, there are disclosed novel pyrimidine 2'-alkylidene nucleosides possessing antiviral activities, in Japanese Patent First Publication 1988-258818, anticancer agents comprising 2'-deoxy-2 -methylidenecytidine and its pharmaceutically acceptable salt as active ingredients.

However, the hitherto-known anticancer agents leave much to be desired in respect to therapeutic effect and involve various problems such as side effects. Thus, the development of excellent anticancer agents has been strongly desired from various fields.

Furthermore, most of the above-mentioned antiviral agents have been accompanied by problems including limited clinical applicability, for example, due to antiviral activity spectra, low absorption, poor solubility, easy decomposition, the advent of drug-fast virus strains, and various side effects. Accordingly, there has been an urgent demand for the development of novel antiviral agents.

SUMMARY OF THE INVENTION

The object of the present invention is to provide novel compounds possessing excellent antitumor and antiviral activities.

This inventors have conducted extensive studies to develop novel compounds useful as anticancer and antiviral agent and found that pyrimidine 2'-methylidene nucleoside compounds possessed excellent antitumor and antiviral activities which culminated in the completion of the present invention.

This invention relates to pyrimidine 2'-deoxy-2'-methylidene nucleoside compounds of the general formula:

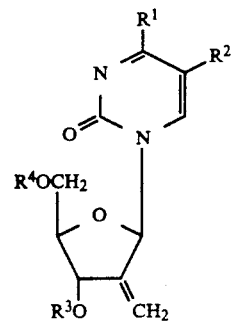

wherein $R^1$ represents amino, hydroxy, silylamino, silyloxy, acylamino or acyloxy; $R^2$ represents hydrogen, halogen, a lower alkyl, a lower alkenyl, a lower alkynyl or a haloalkyl; $R^3$ and $R^4$ represent the same or different hydrogen, silyl, acyl or aminoacyl, except that $R^1$ is amino or hydroxy, and both of $R^3$ and $R^4$ are hydrogen.

In the above-mentioned general formula (I), the acyl in acylamino or acyloxy represented by $R^1$ means straight or branched acyl having 2 to 30 carbon atoms such as acetyl, propionyl, butyryl, pivaloyl, valeryl, hexanoyl, heptanoyl, octanoyl, nanoyl, decanoyl, undecanoyl, dodecanoyl (lauroyl), tridecanoyl, tetradecanoyl (myristoyl), pentadecanoyl, heptadecanoyl (palmitoyl), octadecanoyl (stearoyl), nonadecanoyl, icosanoyl and behenoyl; the acyl in $R^3$ and $R^4$ has the same meaning mentioned above, the aminoacyl means glycinyl, alanyl, isoleucinyl and valyl; the silyl in silylamino or silyloxy represented by $R^1$, or in $R^3$ and $R^4$ means trimethylsilyl, dimethylisopropylsilyl, methyldiisopropylsilyl, triisopropylsilyl, tert-butyldimethylsilyl, tert-butyldiphenylsilyl or the like; and with reference to $R^2$, the halogen means fluorine, chlorine, bromine or iodine; the lower alkyl means methyl, ethyl, propyl, isopropyl, butyl, isobutyl, tert-butyl or the like; the lower alkenyl means vinyl, allyl, 1-propenyl, 2-propenyl, 1-butenyl, 2-butenyl, 3-butenyl or the like; the lower alkynyl means ethynyl, 1-propynyl, 2-propynyl, 1-butynyl, 2-butynyl, 3-butynyl or the like; and the haloalkyl means chloromethyl, bromomethyl, fluoromethyl, iodomethyl, iodoethyl, trifluoroethyl, trifluoropropyl or the like (wherein alkyl chain may optionally has unsaturated bond).

As the salts of the compounds of the general formula (I) of the present invention, in case where $R^1$ is amino, mention is made of acid addition salts such as inorganic salts exemplified by hydrochlorides, sulfates, hydrobromides and phosphates, or organic salts exemplified by maleates, fumarates, tartarates, succinates, citrates methanesulfonates and p-toluenesulfonates.

The present invention encompasses hydrates or other solvates of the compounds of the general formula (I) or their salts.

In the case of the compounds of the general formula (I) wherein $R^1$ is hydroxy group, the present invention encompasses the uridine compounds which are the tautomers represented by the general formula (I'):

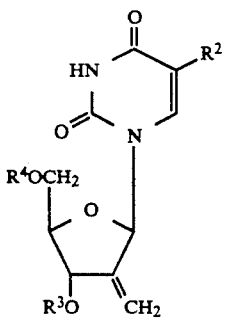

(I')

wherein $R^2$ has the same meaning as above, $R^3$ and $R^4$ are the same or different hydrogen, silyl, acyl or aminoacyl, except that both of $R^3$ and $R^4$ are hydrogen.

As the compounds of the general formula (I), there can be exemplified compounds or their salts whose at least one of 4,3'- and/or 5'-position of the following compounds is acylated or silylated: 2'-methylidenethymidine, 2'-deoxy-2'-methylidenecytidine, 2'-deoxy-2'-methylidene-5-fluorouridine, 2'-deoxy-2'-methylidene-5-chlorouridine, 2'-deoxy-2'-methylidene5-bromouridine, 2'-deoxy-2'-methylidene-5-iodouridine, 2'-deoxy-2'-methylidene-5-fluorocytidine, 2'-deoxy-2'-methylidene5-chlorocytidine, 2'-deoxy-2'-methylidene-5-bromocytidine, 2'-deoxy-2'-methylidene-5-iodocytidine, 2'-deoxy-2'-methylidene-5-methylcytidine, 2'-deoxy-2'-methylidene-5-ethylcytidine, 2'-deoxy-2'-methylidene-5-ethyluridine or 2'-deoxy-2'-methylidene-5-ethylyuridine.

The compounds of the general formula (I) of the present invention can be produced by reacting a compound of the general formula (II):

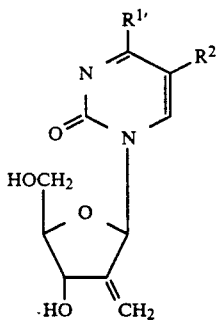

(II)

wherein $R^{1'}$, represents amino or hydroxy, $R^2$ has the same meaning above, or a compound of the general formula (II) protected by a protecting group at optional position(s) except for position(s) which is intended to introduce a silyl or an acyl with silylating agent or acylating agent, and then, if necessary, by removing the protecting group, if desired, followed by making its salt.

The compounds (II) are described in European Patent Application 0 310 673, and Japanese Patent First Publication 1988-258818, among which an optimal one can be selected by taking into consideration the easiness of preparation and handling, reaction yield, intended compound and the like.

As protective groups for the hydroxy groups at 5'- and/or 3'-position of the compounds (II), any protective groups that are conventionally used as the protective groups for hydroxy groups can be applied. As such protective groups, for example, mention can be made of silyl groups such as trimethylsilyl, tert-butyldimethylsilyl, methyldiisopropylsilyl, triisopropylsilyl and tetraisopropyldisiloxyl (TIPDS).

The introduction of the protecting groups can be carried out in accordance with conventional methods. For example, in case of silyl group, it is carried out by using a silylating agent of 1~3-fold mols per mol of the compounds (II) in a basic solvent such as pyridine or the like at a temperature of 0°-50° C.

The acylating agent is reactive derivative of the aliphatic acid having acyl group to be introduced and includes, for example, acid halides of an aliphatic acid such as acid chlorides, acid bromides; acid anhydrides; activated esters or activated acid amides, etc. Particularly preferred are acid halides and acid anhydrides.

The acylation reaction can be carried out in an amount of 1~2-fold mols of the reactive derivative of an aliphatic acid per mol of the compound (II) or its protected compound for 1-50 hours at 10°-50° C., preferably 20°-30° C. in a reaction solvent. It is preferable that the reaction is carried out under ice cooling (0°-10° C.) to prevent heat generation in the beginning of the reaction.

The reaction solvent includes, for example, basic solvents such as trimethylamine, triethylamine, tributylamine, pyridine, picoline, N-methylmorphorine, 2,6-lutidine, and diethylaniline; ethers such as ethylether, tetrahydrofuran, dioxane, or the like; halogenated hydrocarbons such as methylene chloride, chloroform, carbon tetrachloride or the like; aromatic hydrocarbons such as benzene, toluene or the like; amides such as dimethylformamide, diethylacetoamide, formamide or the like; dimethylaminopyridine. The foregoing solvents can be used alone or in combination.

In the process of this invention, where 4-position alone is to be acylated or 4-position and other positions than 4-position are to be introduced with acyl groups, a preferred solvent which can be used includes basic solvents or mixture solvents of basic solvents and other solvents.

In introducing acyl groups at other position(s) than 4-position, it is preferred that 1~2-fold mols, based on 1 mol of the starting material (the compound (II)), of an inorganic acid (e.g., hydrochloric acid, sulfuric acid) or an organic acid (e.g., carboxylic acids such as cyanoacetic acid, chloroacetic acid, fluoroacetic acid, bromoacetic acid, pyruvic acid, 2-chloropropionic acid, 2,4-dichlorobenzoic acid) is incorporated in the reaction solution, or salts of compounds (II) as a starting material and other reaction solvents than basic solvents are used.

The removal of the protecting groups may be carried out by selecting suitably conventional methods. For example, silyl group can be removed by ammonium fluoride treatment.

The silylation reaction may be carried out by the same methods as the reaction of introducing protective groups for hydroxy groups mentioned above. The silylating agents which can be used includes silylhalides such as trimethylsilylchloride, dimethylisopropylchloride, methyldiisopropylsilylchloride, triisopropylsilylchloride, tert-butyldimethylsilylchloride or tert-butyldiphenylsilylchloride etc.

The compounds of this invention thus synthesized can be isolated and purified by recrystallization, absorption chromatography on silica gel or ion exchange chromatography and the like.

The compounds or their salts of this invention can be prepared into medicaments by mixing an effective amount of the compounds (I) or their salts and pharmaceutically acceptable carriers, excipients, diluents and the like. The medicaments can assume various forms such as powders, granules, tablets, sugar-coated tablets, capsules, syrups, suppositories, medicines for external use, injections and medicines for instillation or oral administration. The dosage varies depending on the disease to be treated, the administration route, the preparation form, and the daily dosage is generally 10–400 mg/kg body weight, preferably 50–200 mg/kg body weight, in the case of medicines for oral administration whereas the daily dosage of injections is in the range of 1–10 mg/kg body weight, preferably 1–5 mg/kg body weight. The administration frequency can be chosen in the range of once to four times a day.

The compounds of this invention or salts thereof exhibit significant proliferation inhibitory effects against various types of incubated tumor cells, and has long duration of effects with lower toxicity, thereby to potentiate the effect of the compounds of general formula (II). Therefore, these are useful as an anticancer agent.

They also exhibit antiviral activities against herpes simplex (HSV) and cytomegalovirus (CMV). They are clinically used for the treatment of viral infections.

Example 1:
2'-DEOXY-2'-METHYLIDENE-N⁴-STEAROYL-CYTIDINE

2'-Deoxy-2'-methylidenecytidine, 239 mg, was dissolved in 5 ml of pyridine, and, to the solution was added dropwise 0.63 ml of trimethylsilylchloride under ice cooling. The mixture was stirred at room temperature for 15 minutes, and then 1.7 ml of stearoyl chloride was added dropwise to the mixture under ice cooling followed by stirring at room temperature for 2 hours. After the reaction, 2 ml of water was added to the reaction solution to conduct stirring at room temperature for 5 minutes. Then 2 ml of concentrated ammonia water was added to the solution and stirring was effected for 15 minutes to complete the reaction. Thereafter, the solution was partitioned with chloroform, and the chloroform layer was distilled off under reduced pressure. The residue was treated with a silica gel chromatography (elution solvent chloroform: methanol=2.5:1) to give 200 mg of the objective compound. Yield: 39.6%, m.p.: 116°–120° C.
NMR (CDCl₃)
7.92 (1H, d, J=7.6Hz, 6-H), 7.44 (1H, d, J=7.6Hz, 5-H), 6.55 (1H, s, 1'-H), 5.54 (1H, s, 2'-methylidene), 5.46 (1H, s, 2'-methylidene), 2.43 (2H, t, J=7.3Hz,

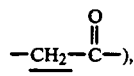

1.25–1.30 (30H, bs, methylene), 0.88 (3H, t, J=6.8Hz, methyl)
IR (KBr) 1640 cm⁻¹ (amido)
UV λmax (in methanol) 250, 301 (nm)

Example 2:
2'-DEOXY-2'-METHYLIDENE-N⁴-DECANOYL-CYTIDINE

2'-Deoxy-2'-methylidenecytidine, 239 mg, was dissolved in 5 ml of pyridine, and to the solution was added dropwise 0.63 ml of trimethylsilyl chloride under ice cooling. The mixture was stirred at room temperature for 5 minutes and then 0.83 ml of decanoyl chloride was added dropwise to the mixture under ice cooling, followed by stirring at room temperature for 2 hours. After the reaction, 2 ml of water was added to the reaction solution, stirring was conducted at room temperature for 5 minutes, and then 2 ml of concentrated ammonia water was added to the solution, followed by stirring for 15 minutes. After the reaction, the solution was partitioned with chloroform, and the chloroform layer was distilled off under reduced pressure. The residue was treated with a silica gel chromatography (elution solvent-chloroform: methanol=25:1) to give 179 mg of the objective compound as an oleaginous product.
Yield: 45.6%
NMR (CDCl₃)
9.25 (1H, bs, NH), 7.93 (1H, d, J=7.6Hz, 6-H), 7.45 (1H, d, J=7.6Hz, 5-H), 6.56 (1H, s, 1'-H), 5.54 (1H, s, 2'-methylidene),
5.45 (1H, s, 2'-methylidene), 2.44 (2H, t, J=7.3Hz,

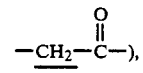

1.1–1.4 (14H, bs, methylene), 0.88 (3H, t, J=6.8Hz, methyl)
UV λmax (in methanol) 250, 301 (nm)

Example 3:
2'-DEOXY-METHYLIDENE-5'-O-STEAROYL-CYTIDINE

2'-Deoxy-2'-methylidenecytidine.HCl, 552 mg, was dissolved in 5 ml of dimethylformamide, to this was added dropwise 670 mg of stearoyl chloride under ice cooling, and stirring was conducted at room temperature overnight. After the reaction, the reaction solution was neutralized with aqueous saturated solution of sodium bicarbonate and partitioned with chloroform. The chloroform layer was distilled off under reduced pressure and the residue so obtained was treated with silica gel chromatography (elution solvent-chloroform: methanol=19:1) to give 380 mg of the objective compound. Yield: 37.6%, m.p.: 104°–105° C.
NMR (CDCl₃)
7.30 (1H, d, J=7.6Hz, 6-H), 6.73 (1H, s, 1'-H), 5.78 (1H, d, J=7.6Hz, 5-H), 5.51 (1H, s, 2'-methylidene), 5.32 (1H, s, 2'-methylidene), 2.33 (2H, t, J=7.7Hz,

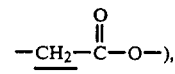

1.30–1.25 (30H, bs, methylene), 0.88 (3H, t, J=6.7Hz, methyl)
IR (KBr) 1725 cm⁻¹ (5'-ester moiety) UV λmax (in methanol) 242, 271 (nm)

Example 4:
5'-O-DECANOYL-2'-DEOXY-2'-METHYLIDENECYTIDINE

2'-Deoxy-2'-methylidenecytidine.HCl, 552 mg, was dissolved in 5 ml of dimethylformamide, to this was added dropwise 420 mg of decanoyl chloride under ice cooling, and stirring was conducted at room temperature overnight. After the reaction, the reaction solution was neutralized with aqueous saturated solution of sodium bicarbonate and partitioned with chloroform. The chloroform layer was distilled off under reduced pressure and the residue thus obtained was treated with silica gel chromatography (elution solvent-chloroform: methanol=10:1) to give 310 mg of the objective compound. Yield: 39.5%, m.p. 104°–109° C.
NMR (CDCl₃)
7.29 (1H d J=7.3Hz 6-H) 6.72 (1H s 1'-H) 5 81 (1H, d, J=7.3Hz, 5-H), 5.50 (1H, s, 2'methylidene), 5.30 (1H, s, 2'-methylidene), 2.33 (2H, t, J=7.6Hz,

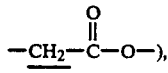

1.15–1.35 (14H, bs, methylene), 0.87 (3H, t, J=7.0Hz, methyl)
IR (KBr) 1725 cm⁻¹ (5'-ester moiety)
UV λmax (in methanol) 243, 270 (nm)

Example 5:
5'-O-BUTYRYL-2'-DEOXY-METHYLIDENECYTIDINE

2'-Deoxy-2'-methylidenecytidine.HCl, 552 mg, was dissolved in 5 ml of dimethylformamide, to this was added dropwise 230 mg of butyryl chloride under ice cooling, and stirring was conducted at room temperature overnight. After the reaction, the reaction solution was neutralized with aqueous saturated solution of sodium bicarbonate and the solvent was distilled off under reduced pressure. The residue was treated with silica gel chromatography (elution solvent-chloroform: methanol=10:1) to give 241.6 mg of the objective compound as oleaginous product. Yield: 39.1%
NMR (DMSO-d₆)
7.38 (1H, d, J=7.3Hz, 6-H), 7.26 (2H, bs, 4-NH₂), 6.52 (1H, s, 1'-H), 5.81 (1H, d, J=7.3Hz, 5-H), 5.72 (1H, d, J=7.6Hz, 3'-OH), 5.34 (1H, s, 2'-methylidene), 5.16 (1H, s, 2'-methylidene), 2.31 (2H, t, J=7.3Hz,

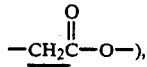

1.54 (2H, m, J=7.3Hz, CH₃—CH₂—CH₂—), 0.88 (3H, t, J=7.3Hz, methyl)
UV λmax (in methanol) 242, 270 (nm)

The following compounds were prepared in the same manner as in Example 5:
5'-O-Myristoyl-2'-deoxy-2'-methylidenecytidine m.p. 123°–125° C.
5'-O-Palmitoyl-2'-deoxy-2'-methylidenecytidine m.p. 106°–112° C.
5'-O-Heptadecanyl-2'-deoxy-2'-methylidenecytidine m.p. 75°–85° C.
5'-O-Behenoyl-2'-deoxy-2'-methylidenecytidine m.p. 98°–102° C. Example 7: 5'-O-t-Butyldiphenylsilyl-2'-deoxy-2'-methylidenecytidine 2'-Deoxy-2'-methylidenecytidine.HCl, 549 mg (2 mM), was dissolved in 3 ml of dimethylformamide and to this were added 449 mg (6.6 mM) and 605 mg (2.2 mM), followed by stirring at room temperature for 3 hours. After the reaction, the solvent was distilled off and the residue obtained was partitioned with chloroform and aqueous saturated solution of ammonium chloride. The organic layer wa distilled off under reduced pressure, and the resulting residue was treated with silica gel chromatography (elution solvent: 5% methanol-chloroform) to give 893 mg of the objective compound. Yield 87% Anal. for C₂₆H₃₁N₃Si
Calcd. (%): C, 65.38; H, 6.49; N, 8.80
Found (%): C, 65.25; H, 6.50; N, 8.80

Example 8

5'-O-tert-Butyldimethylsilyl-2'-methylidenecytidine of m.p. 139°–151° C. was prepared in a similar procedure to

Example 7

Anal. for C₁₆H₂₇N₃O₄Si
Calcd. (%) : C, 54.36; H, 6.49; N, 11.89
Found (%) : C, 54.52; H, 7.68; N, 11.88

Example 9:
N⁴,5'-O-Distearoyl-2'-deoxy-2'-methylidenecytidine

2'-Deoxy-2'-methylidenecytidine, 239 mg, was dissolved in 5 ml of pyridine, 1.7 ml of stearoyl chloride was added portionwise under ice cooling, and the solution was stirred for 15 minutes. After the reaction, the reaction solution was partitioned with chloroform and the chloroform layer was distilled off under reduced pressure. The resulting residue was treated with silica gel chromatography (elution solvent: a mixture solvent of chloroform and methanol) to give the objective compound. m.p. 135°–139° C.

Example 10

N⁴,3',5'-O-Tristearoyl-2'-deoxy-2'-methylidenecytidine was prepared in a similar procedure to Example 9. m.p. 92°–96°

Example 11:
N⁴,3'-O-Diacetyl-2'-deoxy-2'-methylidenecytidine

5'-O-t-Butyldiphenylsilyl-2'-deoxy-2'-methylidenecytidine, 843 mg (1.64 mM) was 10 ml of pyridine, 1.5 ml of acetic anhydride was added thereto, and the mixture was stirred at room temperature for 1 hour.

Water was added to the reaction solution to stop reaction, and then, the solvent was distilled off under reduced pressure. The resulting residue was partitioned with a mixture solvent of diethylether and aqueous saturated solution of sodium bicarbonate and the organic layer was distilled off to give a crude product of 5'-O-t-butyldiphenylsilyl-N⁴,3'-O-diacetyl2'-deoxy-2'-methylidenecytidine in an amount of 870 mg (yield: 89%).

The crude product, 547 mg (1.7 mM), was dissolved in 10 ml of tetrahydrofuran and 2 ml (1 molar solution) of n-butylammonium fluoride was added thereto, followed by stirring at room temperature for 15 minutes.

After neutralization with acetic acid, the solvent was distilled off under reduced pressure and the residue so obtained was treated with silica gel chromatography (elution solvent: 5% methanol-chloroform) to give 447 mg of N⁴,3'-O-diacetyl-2'-deoxy-2'-methylidenecytidine as crystal. Yield, 82%; m.p. 174°–175° C.

The following compounds can be prepared in a similar manner to Examples above. 12) 5'-O-(2-Amino-3-methylbutyryl)-2'-deoxy-2'-methylidenecytidine 13) 5'-O-(2-Amino-4-methylvaleryl)-2'-deoxy-2'-methylidenecytidine 14) 5'-O-(2-Amino-3-methylvaleryl)-2'-deoxy-2'-methylidenecytidine 15) 5'-O-(2-Aminopropionyl)-2'-deoxy-2'-methylidenecytidine 16)

3'-O,N⁴-Ditrimethylsilyl-2'-deoxy-2'-methylidenecytidine
17) N⁴,3',5'-O-Trimethylsilyl-2'-deoxy-2'-methylidenecytidine
18) 3'-O or 5'-O,N⁴-Dimethyldiisopropylsilyl-2'-deoxy-2'-methylidenecytidine
19) N⁴,3',5'-O-Trimethyldiisopropylsilyl-2'-deoxy-2'-methylidenecytidine
20) 3'-O or 5'-O,N⁴-Ditriisopropylsiyl-2'-deoxy-2'-methylidenecytidine
21) N⁴,3',5'-Triisopropylsilyl-2'-deoxy-2'-methylidenecytidine

| Pharmaceutical Preparation Example 1: Tablets | |
|---|---|
| 2'-Deoxy-2'-methylidene-N⁴-stearoylcytidine | 10 g |
| Corn starch | 65 g |
| Carboxymethylcellulose | 20 g |
| Polyvinyl pyrrolidone | 3 g |
| Calcium Stearate | 2 g |
| Total | 100 g |

One tablet (100 mg) containing 10 mg of the active compound is produced by conventional method.

| Pharmaceutical Preparation Example 2: Fine Powder, Capsules | |
|---|---|
| 2'-Deoxy-2'-methylidene-5-fluoro-N⁴-stearoylcytidine | 20 g |
| Crystalline Cellulose | 80 g |
| Total | 100 g |

Both ingredients were admixtured to make fine powder, 100 mg of which is encapsulated with No. 5 hard capsules.

Pharmacological Experiment

L-1210 ($1 \times 10^5$) leukemia cells were transplanted intraperitoneally into three female CD2F$_1$ mice (8 weeks age). Test compounds of 25 mg/kg were administered intraperitoneally once a day for five successive days from the next day of the transplantation.

Antitumor efficacy against L-1210 was expressed as a percentage of the mean survival time (MST) of the control group after measuring MST:

$$T/C = \frac{MST \text{ of the test group}}{MST \text{ of the control group}} \times 100 \ (\%)$$

The T/C value of the compound in Example 3 at a dose of 25 mg/kg was 243% whereas the T/C value of 2'-deoxy-2'methylidenecytidine at the same dose was 152%.

We claim:
1. A pyrimidine 2'-deoxy-2'-methylidene nucleoside compound of the formula:

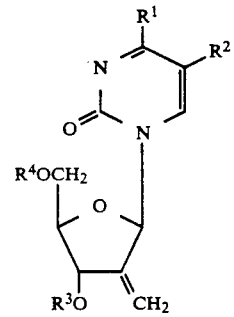

wherein $R^1$ represents amino or hydroxy; $R^2$ represents hydrogen, halogen, a lower alkyl, a lower alkenyl, a lower alkynyl or a haloalkyl; $R^3$ and $R^4$ may be the same or different and represent hydrogen, stearoyl or aminoacyl, or a pharmaceutically acceptable salt or hydrate thereof, except that both of $R^3$ and $R^4$ may be hydrogen.

2. A compound or a pharmaceutically acceptable salt or hydrate thereof as claimed in claim 1 which is selected from the group consisting of 2'-deoxy-2'-methylidene-5'-O-stearoylcytidine and 5'-O-(2-amino-3-methylvaleryl)-2'-deoxy-2'-methylidenecytidine.

* * * * *

UNITED STATES PATENT AND TRADEMARK OFFICE
CERTIFICATE OF CORRECTION

PATENT NO. : 5,026,835       Page 1 of 2
DATED      : June 25, 1991
INVENTOR(S): Tohru UEDA et al.

It is certified that error appears in the above-indentified patent and that said Letters Patent is hereby corrected as shown below:

Column 7, between lines 50 and 51, insert and center --Example 6:--; and lines 58 and 59, rewrite as follows:

--98°C-102°C.

Example 7:

5'-O-t-Butyldiphenylsilyl-2'-deoxy-2'-methylidenecytidine--.

Column 8, line 10, after "to" insert --Example 7.--; and line 10, delete "Example 7".

line 67, change "wa" to --was--.

UNITED STATES PATENT AND TRADEMARK OFFICE
CERTIFICATE OF CORRECTION

PATENT NO. : 5,026,835
DATED : June 25, 1991
INVENTOR(S) : Tohru Ueda, et al.

It is certified that error appears in the above-indentified patent and that said Letters Patent is hereby corrected as shown below:

Column 10, line 34, after "may" insert --not--.

Signed and Sealed this

Twenty-eighth Day of November 1995

Attest:

BRUCE LEHMAN

Attesting Officer     Commissioner of Patents and Trademarks

UNITED STATES PATENT AND TRADEMARK OFFICE
CERTIFICATE OF CORRECTION

PATENT NO. : 5,026,835
DATED : June 25, 1991
INVENTOR(S) : Tohru UEDA et al.

It is certified that error appears in the above-indentified patent and that said Letters Patent is hereby corrected as shown below:

Column 7, between lines 50 and 51, insert and center --Example 6:--; and lines 58 and 59, rewrite as follows:

--98°-102°C.

Example 7:

5'-O-t-Butyldiphenylsilyl-2'-deoxy-2'-methylidenecytidine--.

Column 7, line 67, change "wa" to --was--.

Column 8, line 10, after "to" insert --Example 7.--; and line 10, delete "Example 7".

UNITED STATES PATENT AND TRADEMARK OFFICE
CERTIFICATE OF CORRECTION

PATENT NO. : 5,026,835
DATED : June 25, 1991
INVENTOR(S) : Tohru Ueda, et al.

It is certified that error appears in the above-indentified patent and that said Letters Patent is hereby corrected as shown below:

Column 10, line 34, after "may" insert --not--.

This certificate supersedes Certificate of Correction issued November 28, 1995.

Signed and Sealed this

Twentieth Day of February, 1996

Attest:

Attesting Officer

BRUCE LEHMAN

Commissioner of Patents and Trademarks